United States Patent [19]

Gohndrone

[11] Patent Number: 5,118,829

[45] Date of Patent: Jun. 2, 1992

[54] PROCESS FOR CYCLOALKYL SUBSTITUTION OF HYDROGEN CONTAINING SILANES

[75] Inventor: John M. Gohndrone, Midland, Mich.

[73] Assignee: Dow Corning Corporation, Midland, Mich.

[21] Appl. No.: 766,300

[22] Filed: Sep. 27, 1991

[51] Int. Cl.$^5$ ................................................ C07F 7/08
[52] U.S. Cl. ........................................ 556/481; 556/478
[58] Field of Search ............................... 556/481, 478

[56] References Cited

U.S. PATENT DOCUMENTS

| | | | |
|---|---|---|---|
| 2,572,302 | 10/1951 | Barry | 556/481 |
| 2,576,448 | 11/1951 | Daudt | 556/481 |
| 2,594,860 | 4/1952 | Brewer | 260/448.2 |
| 2,600,198 | 6/1952 | Brewer | 556/481 |
| 2,611,775 | 9/1952 | Barry | 556/481 |
| 2,626,266 | 1/1953 | Barry | 556/481 |
| 2,626,267 | 1/1953 | Barry | 556/481 |
| 2,660,597 | 11/1953 | Shafer | 260/448.2 |
| 2,775,606 | 12/1956 | Wagner | 260/448.2 |

FOREIGN PATENT DOCUMENTS 0505648  6/1976  U.S.S.R. .............................. 556/581

OTHER PUBLICATIONS

Wright J. Organometallic Chem. 145:307–314 (1978).

Primary Examiner—Paul F. Shaver
Attorney, Agent, or Firm—William F. Boley

[57] ABSTRACT

The present invention is a process for substituting cycloalkyl substituents for a silicon bound hydrogen of a silane. The process employs a preformed organoborane compound as a catalyst to increase the apparent rate of the reaction and to increase the yield of desired cycloalkylsilanes.

20 Claims, No Drawings

PROCESS FOR CYCLOALKYL SUBSTITUTION OF HYDROGEN CONTAINING SILANES

BACKGROUND OF INVENTION

The present invention is a process for substituting cycloalkyl substituents for a silicon bound hydrogen of a silane. The process employs an organoborane compound as a catalyst to increase the apparent rate of the reaction and to increase the yield of desired cycloalkyl substituted silanes.

Barry, U.S. Pat. No. 2,626,266, issued Jan. 20, 1953, describes a process where a benzenoid hydrocarbon is reacted with trichlorosilane in the presence of a boron halide, at a temperature above 230° C., and under sufficient pressure that at least a portion of the reaction mixture is in a condensed phase. Under these conditions, aromatic halosilanes are reported to constitute a major portion of the reaction product. Barry discloses that the boron halide may be added in the form of boron trichloride or trifluoride, or it may by produced in situ by the addition of a material such as boric acid. Typical reaction times for the process were 16 to 17 hours.

Barry, U.S. Pat. No. 2,572,302. issued Oct. 23. 1951, describes a process where an organodichloromonohydrosilane, for example methyldichlorosilane, is reacted with benzene in the presence of a boron halide, at a temperature above 150° C. and under sufficient pressure that at least a portion of the reaction mixture is in a condensed phase. Under these conditions, the organodichlorosilyl derivatives of the hydrocarbon are reported to constitute a major portion of the reaction product. Barry discloses that the boron halide may be added in the form of boron trichloride or trifluoride, or it may be produced in situ by the addition of materials such as boric acid. A typical reaction time for the process was 26 hours.

Brewer. U.S. Pat. No. 2,594,860, issued Apr. 29. 1952. describes a process for making phenyltrichlorosilane by reacting a mixture comprising benzene, dichlorosilane, and silicon tetrachloride in the presence of a boron halide as a catalyst. Brewer states that the reaction is preferably conducted in a pressure reactor, under 750 psi to 2500 psi pressure, at temperatures ranging from about 250° C. to below the decomposition point of either the reactants or the reaction product. Brewer discloses that the boron halide can be boron trichloride or boron trifluoride or its etherate. The reported time for the reaction was four hours.

Wagner, U.S. Pat. No. 2,775,606, issued Dec. 25, 1956, describes a process where benzene is reacted with a mixture of dichlorosilane and trichlorosilane to produce a product which is principally phenyldichlorosilane. The preferred pressure range for the process is 1,000 psi to 4,000 psi and the preferred temperature range is 300° C. to 500° C. Wagner states that the use of a catalyst results in a decreased reaction time and permits a rapid flow process. Contact times of 2-12 hours are reported for the static process and a calculated contact time of about one minute for a rapid flow process. Wagner reports Lewis acid catalysts of the metal halide type such as BCl$_3$, CbCl$_5$, and AlCl$_3$ to be effective in the process.

Brewer. U.S. Pat. No. 2,600,198 issued Jun. 10, 1952, described a process where an aromatic hydrocarbon and a halosilane, containing at least one silicon-bonded hydrogen, are reacted in the presence of a Friedel-Crafts type catalyst, for example trichloroboron. Brewer states that if product silane is removed along with substantially all the evolved hydrogen and to the residue is added an additional amount of aromatic hydrocarbon and halosilane, the newly added reactants are again caused to react and that a greatly increased conversion of the newly added reactants to aromatic halosilanes can be realized. Brewer states that under the described conditions the reaction can be effected in about 3 to 30 minutes.

Wright, Journal of Organometallic Chemistry, 145: 307-314 (1978), reported on studies to determine the role of boron trichloride in the synthesis of phenyltrichlorosilane from benzene and trichlorosilane. Wright concluded that phenylboranes play an important role in the catalyst and that the reduction of boron trichloride was a slow process accounting for the induction period observed in the reaction of benzene with trichlorosilane.

Shafer, et al., U.S. Pat. No. 2,660,597 issued Nov. 24, 1953, describes the reaction of trichlorosilane with cyclohexane in the presence of boron trichloride catalyst. The reaction was run at 375° C. for 14 hours. The reported yield for a six carbon atom alkyl chlorosilane was 13 weight percent.

The inventors have found that the presence of at least one organic substituent on boron compounds, described herein, provides a catalyst which can increase the apparent reaction rate and the product yield of the reaction of cycloalkanes with hydrogen containing halosilanes. The use of the organic substituted boron catalysts allows the process to be run at lower temperatures and shorter residence times, than those described by the above cited art. The shorter residence times and lower temperatures reduce undesirable reactions and the heat induced decomposition of reactants and products.

SUMMARY OF INVENTION

The present invention is a process for substituting cycloalkyl substituents for a silicon bound hydrogen of a silane. The process employs an organoborane compound as a catalyst to increase the apparent rate of the reaction and to increase the yield of desired cycloalkylsilanes.

DESCRIPTION OF INVENTION

The present invention is a process for preparing cycloalkylsilanes of formula $$R^1{}_a R^2{}_d H_{b-d} SiX_{4-a-b},$$ 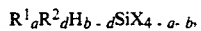

where each $R^1$ is independently selected from a group consisting of alkyl radicals of 1 to 7 carbon atoms, aryl radicals, and $R^2$; $R^2$ is a cycloalkyl radical of formula $$R^3{}_y C_n H_{2-y-1},$$ 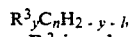

where $R^3$ is selected from a group consisting of alkyl radicals of 1 to 7 carbon atoms and aryls, y=0 or 1, and n is an integer from 4 to 7; each X is independently selected from a group consisting of chloride, bromide, and fluoride atoms a=0 or 1, b=1 or 2, d is an integer in a range of 1 to b, and a+b=1, 2, or 3.

The process comprises: contacting a cycloalkane of formula $$R^3{}_y C_n H_{2n-y},$$ 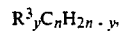

where $R^3$, n, and y are as previously described; with a silane of formula $R^1{}_nH_bSiX_{4-a-b}$ where $R^1$, a, b, and X are as previously described; in the presence of an organoborane catalyst of formula $R^1{}_cBX_{3-c}$.

where $R^1$ and X are as previously described and $c < 1, 2,$ or 3; at a temperature within a range of about 200° C. to 500° C. and a pressure within a range of about 1000 psi to 5000 psi.

The present process substitutes a cycloalkyl group for a hydrogen substituent of a silane. The substitution is effected by contacting a cycloalkane with a silane in the presence of an organoborane catalyst.

The cycloalkane can be, for example, cyclobutane, cyclopentane, cyclohexane, and cycloheptane. The cycloalkane can be substituted with an organic radical, $R^3$, where $R^3$ is selected from the group consisting of alkyl radicals of 1 to 7 carbon atoms and aryl radicals. $R^3$ can be, for example, methyl, ethyl, propyl, butyl, isobutyl, tert-butyl, heptyl, phenyl, tolyl, and xylyl. The organic substituted cycloalkane can be, for example, methylcyclopentane and benzylcyclohexane.

The silane can be a halosilane or an organohalosilane. The halosilane can be, for example, trichlorosilane, dichlorosilane, tribromosilane, dibromosilane, and trifluorosilane. The organohalosilane is substituted with a hydrocarbon radical, $R^1$, where $R^1$ is selected from a group consisting of alkyl radicals of 1 to 7 carbon atoms, aryl radicals, and the cycloalkyl radical $R^2$. The alkyl hydrocarbon radical can be, for example, methyl, ethyl, propyl, butyl, isobutyl, tert-butyl, and heptyl. The aryl hydrocarbon radical can be, for example, phenyl, tolyl, and xylyl. The cycloalkyl radical, $R^2$, can be, for example, cyclobutyl, cyclopentyl, methylcyclopentyl, cyclohexyl, benzylcyclohexyl, and cycloheptyl.

The mole ratio of cycloalkane to silane employed in the process will depend upon the number of hydrogens substituted on the silicon atom of the silane and the desired substitution. In general, it is preferred that the mole ratio of cycloalkane to hydrogen bound to the silicon of the silane be within a range of about 0.5 to 6.0. More preferred is when the mole ratio of cycloalkane to hydrogen bound to the silicon of the silane is within a range of about 1.0 to 1.1. A lower mole ratio of reactants may be employed, but may result in unacceptable low yields of cycloalkyl substituted silanes. A higher mole ratio than 6.0 may be employed, but to no perceived advantage.

The catalyst employed in the present invention is an organoborane compound containing one, two, or three hydrocarbon radicals, $R^1$, as previously described. The organoborane compound may be preformed or formed in situ. The organoborane catalyst can contain one or two halogen atoms, X, selected from the group consisting of chloride, bromide, and fluoride. The organoborane catalyst can be, for example, methyldichloroborane, dimethylchloroborane, trimethylchloroborane, methyldibromoborane, dimethylbromoborane, ethyldichloroborane, diethylchloroborane, triethyldichloroborane, phenyldichloroborane, diphenylchloroborane, triphenylborane, phenyldibromoborane, diphenybromoborane, diphenylfluoroborane, methylpentyldichloroborane, benzylhexyldichloroborane, and tricyclopentylborane.

The hydrocarbon radical(s) substituted on the organoborane catalyst can be the same or different than the hydrocarbon radical(s) to be substituted on the silane by reaction with the cycloalkane. Preferred, is when the hydrocarbon radical(s) substituted on the organoborane catalyst is the same as that to be substituted on the silane by reaction with the cycloalkane.

An effective concentration of organoborane catalyst is within a range of about 0.1 to 6.0 weight percent, based upon the combined weights of the cycloalkane, the silane, and the organoborane catalyst fed to the reactor. A preferred concentration for the organoborane catalyst is within a range of about 1.0 to 3.0 weight percent.

The temperature at which the process can be run is within a range of about 200° C. to 500° C. A preferred temperature for running the process is within a range of about 275° C. to 375° C. The temperature can be controlled by standard means for heating reactors, for example, a heating mantle or a heating jacket through which a heat transfer fluid is circulated.

The present process must be run under sufficient pressure to assure that at least a portion of the cycloalkane, silane, and organoborane catalyst are in a liquid phase. A useable pressure for running the process is within a range of about 1000 psi to 5000 psi. A preferred pressure for running the process is within a range of about 1000 psi to 2000 psi.

The present process can be run as a batch process or as a continuous process, in standard high pressure reactors. Preferred is a continuous process. When the process is run as a batch process, residence times for the reaction to occur are within a range of about 0.1 to 6.0 hours. A preferred residence time for the batch process is within a range of about 0.25 to 3.0 hours. When the present process is run as a continuous process, the residence time may be shortened as much as a factor of two to ten, in comparison to the batch process. A preferred embodiment of the present process is when the process is run as a continuous process with a residence time within a range of about one minute to 15 minutes. More preferred is when the present process is run as a continuous process employing a coiled-tube reactor.

Examples of cycloalkyl substituted silanes that may be made by the present process are: cyclobutylchlorosilane, cyclopentylchlorosilane, cyclohexylchlorosilane, cycloheptylchlorosilane, cyclobutyldichlorosilane, cyclopentyldichlorosilane, cyclohexyldichlorosilane, cycloheptyldichlorosilane, cyclobutyltrichlorosilane, cyclopentyltrichlorosilane, cyclohexyltrichlorosilane, cycloheptyltrichlorosilane, dicyclobutyldichlorosilane, dicyclopentyldichlorosilane, dicyclohexyldichlorosilane, dicycloheptyldichlorosilane, cyclopentylbromosilane, cyclohexylbromosilane, cyclopentyltrichlorosilane, cyclohexyltribromosilane, cyclobutylmethylsilane, cyclopentylmethylsilane, cyclohexylmethylsilane, cycloheptylmethylsilane, cyclopentylmethylchlorosilane, cyclohexylmethylchlorosilane, cyclopentylmethyldichlorosilane, cyclohexyldichlorosilane, dicyclopentylmethylsilane, dicyclohexylmethylsilane, dicyclohexylmethylchlorosilane, cyclopentylethylsilane, cyclohexylethylchlorosilane, dicyclobutylethylsilane, cyclopentylphenylsilane, cyclohexylphenylsilane, dicyclopentylphenylchlorosilane, tricyclohexylchlorosilane, methylcyclopentyltrichlorosilane, and benzylcyclohexyltrichlorosilane.

The following examples are offered to facilitate understanding of the present process. These examples are not meant to be limiting on the scope of the claims herein.

EXAMPLE 1

The reaction of cyclohexane with trichlorosilane in the absence of phenyldichloroborane was evaluated. A mixture containing 39 weight percent cyclohexane and 61 weight percent trichlorosilane was placed in a series of glass tubes and the tubes sealed. The tubes were heated to 350° C., at an estimated internal pressure of about 1500 psi, for times of 30, 90, and 260 minutes. At the end of each time period, the tubes were cooled and the contents analyzed by gas chromatography using a flame ionization detector (GC-FID). No significant quantities of cyclohexyl substituted silane products were detected.

EXAMPLE 2

A mixture containing by weight 37.5% cyclohexane, 61.0% trichlorosilane and 1.5% phenyldichloroborane was placed in a series of glass tubes and the tubes sealed. The tubes were heated to 350° C., at an estimated internal pressure of about 1500 psi, for the times given in Table 2. At the indicated time, the tubes were cooled and the contents analyzed by GC-FID. The results are presented as percent area under the curve, as defined by the GC-FID analysis.

TABLE 1

| | Phenyldichloroborane Catalyzed Reaction of Cyclohexane With Trichlorosilane. | | | |
|---|---|---|---|---|
| Time | GC-FID Area Percent | | | |
| (Min.) | $(C_6H_{11})HSiCl_2$ | $(C_6H_{11})SiCl_3$ | $(C_6H_{11})_2SiCl_2$ | $C_6H_{12}$ |
| 0 | 0.00 | 0.00 | 0.00 | 99.70 |
| 30 | 0.87 | 14.72 | 0.10 | 79.65 |
| 60 | 1.50 | 25.62 | 0.87 | 50.48 |
| 120 | 1.22 | 26.16 | 0.90 | 41.25 |
| 180 | 1.01 | 27.46 | 1.08 | 37.05 |

The data demonstrate the short residence time required to achieve an equilibrium limited amount of cyclohexyltrichlorosilane when using phenyldichloroborane as catalyst.

EXAMPLE 3

The effectiveness of various boron compounds as catalyst for the reaction of cyclohexane with trichlorosilane was evaluated. The process was conducted in sealed glass tubes as described in Example 2. Each tube contained by weight 37.5% cyclohexane, 61.0% trichlorosilane, and 1.5% boron compound. The process was conducted at 310° C. and approximately 1500 psi pressure. The results are presented in Table 2.

TABLE 2

| | Effectiveness of Selected Boron Compounds as Catalyst for The Reaction of Cyclohexane With Trichlorosilane Boron Compound | | |
|---|---|---|---|
| | GC-FID Area percent $(C_6H_{11})SiCl_3$ | | |
| Time | $BCl_3$ | $(PhBCl_2)$ | $(C_6H_{11})_3B$ |
| 0 | 0 | 0 | 0 |
| 15 | 0 | — | 14 |
| 30 | 10 | 15 | 28 |
| 60 | 22 | 26 | 30 |
| 90 | 22 | 30 | 30 |

The data presented in Table 2 demonstrate that organic substituted boron compounds can increase both the rate of production of hexyltrichlorosilane and the yield of hexyltrichlorosilane, in comparison to trichloroborane as catalyst.

EXAMPLE 4

Using a procedure similar to that described in Example 2, a mixture containing by weight 44.6% cyclooctane, 53.9% trichlorosilane, and 1.5% phenyldichloroborane was heated for 60 minutes at 350° C., at about 1500 psi pressure. Negligible cyclooctyltrichlorosilane was observed by GC-FID.

EXAMPLE 5

Using a procedure similar to that described in Example 2, a mixture containing by weight 33.5% cyclopentane 64.8% trichlorosilane, and 1.8% phenyldichloroborane was heated at 350° C. and about 1500 psi pressure, for the times presented in Table 3. The results are presented in Table 3.

TABLE 3

| | Phenyldichloroborane Catalyzed Reaction of Cyclopentane With Trichlorosilane. | |
|---|---|---|
| | GC-FID Area Percent | |
| Time (Min.) | $C_5H_9SiCl_3$ | $(C_5H_9)_2SiCl_2$ |
| 15 | 0.8 | — |
| 30 | 10.2 | 0.7 |
| 60 | 24.6 | 1.2 |

EXAMPLE 6

The effectiveness of phenyldichloroborane as a catalyst for the reaction of cyclohexane with methyldichlorosilane was evaluated. The procedure was as described in Example 2. A mixture containing by weight 41.5% cyclohexane, 56.7% methyldichlorosilane, and 1.8& phenyldichloroborane was heated at 350° C. and about 1500 psi pressure. The results are presented in Table 4.

TABLE 4

| | Phenyldichloroborane Catalyzed Reaction of Cyclohexane With Methyldichlorosilane. | |
|---|---|---|
| | GC-FID Area Percent | |
| Time (Min.) | $(C_6H_{11})MeSiCl_2$ | $(C_6H_{11})_2MeSiCl$ |
| 15 | 3.5 | 0.2 |
| 30 | 4.1 | 0.2 |
| 60 | 4.8 | 0.3 |

EXAMPLE 7

The effectiveness of phenyldichloroborane as a catalyst for the reaction of methylcyclopentane with trichlorosilane was evaluated. A mixture containing by weight 54.8% methylcyclopentane, 44.1% trichlorosilane, and phenyldichloroborane was heated at about 330° C. and about 1500 psi pressure, for 60 minutes, in a sealed glass tube. The contents of the seal tube were cooled and analyzed by GC using a thermal conductivity detector (TCD). Methylcyclopentyltrichlorosilane comprised about 3.6% of the area under the curve, as defined by the GC-TCD analysis.

EXAMPLE 8

The effectiveness of phenyldichloroborane as a catalyst for the reaction of cycloheptane with trichlorosilane was evaluated. A mixture containing by weight 58.6% cycloheptane, 40.4% trichlorosilane, and 1.0% phenyldichloroborane was heated at about 330° C. and about 1500 psi pressure, for 120 minutes, in a sealed glass tube. The contents of the seal tube were cooled and analyzed by GC-TCD. Cyclopentyltrichlorosilane comprised about 1.6% of the area under the curve, as defined by the GC-TCD analysis.

EXAMPLE 9

The effectiveness of phenyldichloroborane as a catalyst for the reaction of cyclohexylbenzene with trichlorosilane was evaluated. A mixture containing by weight 69.8% benzylcyclohexane, 29.5% trichlorosilane, and 0.7% phenyldichloroborane was heated at about 330° C. and about 1500 psi pressure, in sealed glass tubes, for the times presented in Table 5. At the end of the appropriate heating period, the contents of the seal tube were cooled and analyzed by GC-TCD. The results are presented in Table 5 as percent area under the curve, as defined by the GC-TCD analysis.

TABLE 5

Phenyldichloroborane Catalyzed Reaction of Benzylcyclohexane With Trichlorosilane.

| Time (Min.) | GC-TCD Area Percent Benzylcyclohexyltrichlorosilane |
|---|---|
| 60 | 0.9 |
| 120 | 6.5 |
| 210 | 9.5 |

EXAMPLE 10

The effectiveness of phenyldichloroborane as a catalyst for the reaction of cyclohexane with trichlorosilane was evaluated in a continuous process. A mixture containing by weight 37.8& cyclohexane, 60.9% trichlorosilane, and 1.3% phenyldichloroborane was prepared. The mixture was fed to a continuous flow reactor comprising a heated ¼ inch stainless steel tube. The reactor was maintained at a temperature of about 350° C. and a pressure of about 1600 psi. Residence time of the feed within the reactor was about 1.5 minutes, for each pass. Product and unreacted feed materials were collected in a cold trap upon exit from the reactor. The collected materials were recycled through the reactor until equilibrium of the reaction mixture was reached. The contents of the cold trap were analyzed after each pass by GC-FID. The results are presented in Table 6 as percent area under the curve, as defined by the GC-FID analysis.

TABLE 6

Phenyldichloroborane Catalyzed Reaction of Cyclohexane With Trichlorosilane in a Continuous Process

| Time (Min.) | GC-FID Area Percent | |
|---|---|---|
| | $(C_6H_{11})SiCl_3$ | $(C_6H_{11})_2SiCl_2$ |
| 1.5 | 1.6 | 0.1 |
| 3.0 | 12.5 | 0.7 |
| 4.5 | 24.7 | 1.3 |
| 6.0 | 26.1 | 1.6 |
| 7.5 | 29.7 | 2.1 |
| 9.0 | 29.2 | 2.1 |

What is claimed is:

1. A process for preparing cycloakylsilanes of formula $$R^1{}_aR^2{}_dH_b{}_-{}_dSiX_{4-a-b}$$

where each $R^1$ is independently selected from a group consisting of alkyl radicals of 1 to 7 carbon atoms, aryl radicals, and $R^2$; $R^2$ is a cycloalkyl radical of formula $$R^3{}_yC_nH_{2n-y-1}$$

where $R^3$ is selected from a group consisting of alkyl radicals of 1 to 7 carbon atoms and aryls, y=0 or 1, and n is an integer from 4 to 7; each X is independently selected from a group consisting of chloride, bromide, and fluoride atoms, a=0 or 1, b=1 or 2, d is an integer in a range of 1 to b, and a+b=1, 2, or 3; the process comprising: contacting a cycloalkane of formula $$R^2{}_yC_nH_{2n-y}$$

where $R^3$, n, and y are as previously described; with a silane of formula $$R^1{}_aH_bSiX_{4-a-b}$$

wherein $R^1$, a, b, and X are as previously described; in the presence of an organoborane catalyst of formula $$R^1{}_cBX_{3-c}$$

where $R^1$ and X are as previously described and c=1, 2, or 3; at a temperature within a range of about 200° C. to 500° C. and a pressure within a range of about 1000 psi to 5000 psi.

2. A process according to claim 1, where n is 5 or 6.
3. A process according to claim 1, wherein a is zero and b is 1.
4. A process according to claim 1, where $R^1$ is methyl.
5. A process according to claim 1, where X is chloride.
6. A process according to claim 1, where the cycloalkane is selected from a group consisting of cyclopentane, cyclohexane, cycloheptane, methylcyclopentane, and benzylcyclohexane.
7. A process according to claim 1, where the process is run as a continuous process.
8. A process according to claim 1, where c is one.
9. A process according to claim 1, where the temperature is within a range of about 275° C. to 375° C.
10. A process according to claim 1, where the pressure is within a range of about 1000 psi to 2000 psi.
11. A process according to claim 1, where the mole ratio of the cycloalkane to hydrogen present on the silicon atom of the silane is within a range of 0.5 to 6.0.
12. A process according to claim 1, where the mole ratio of the cycloalkane to hydrogen present on the silicon atom of the silane is within a range of 1.0 to 1.1.
13. A process according to claim 1, where concentration of the organoborane catalyst is within a range of about 0.1 to 6.0 weight percent, based upon combined weights of the cycloalkane, the silane, and the organoborane catalyst.
14. A process according to claim 1, where concentration of the organoborane catalyst is within a range of about 1.0 to 3.0 weight percent, based upon combined weights of the cycloalkane, the silane, and the organoborane catalyst.
15. A process according to claim 1, where the $R^1$ substituted on the organoborane catalyst is of the same formula as the cycloalkyl radical to be substituted on the silane.
16. A process according to claim 1, where the organoborane catalyst is selected from a group consisting of phenyldichloroborane, diphenylchloroborane, and triphenylborane.
17. A process according to claim 1, where the organoborane catalyst is phenyldichloroborane.
18. A continuous process according to claim 7, where residence time is within a range of about one minute to 15 minutes.
19. A process according to claim 1, where the process is run as a batch process and residence time is within a range of about 0.25 hours to 3.0 hours.
20. A process according to claim 1, where the organoborane catalyst is preformed, prior to addition to the process.

* * * * *